United States Patent [19]
Viera

[11] Patent Number: 5,807,279
[45] Date of Patent: Sep. 15, 1998

[54] GUIDEWIRE HAVING RADIOPAQUE DISTAL TIP

[75] Inventor: Fernando M. Viera, Hialeah, Fla.

[73] Assignee: Cordis Corporation, Miami Lakes, Fla.

[21] Appl. No.: 714,935

[22] Filed: Sep. 27, 1996

[51] Int. Cl.$^6$ .................................................. A61B 5/00
[52] U.S. Cl. ............................................................ 600/585
[58] Field of Search ................................ 128/657, 658, 128/772; 604/280–282

[56] References Cited

U.S. PATENT DOCUMENTS

| | | | |
|---|---|---|---|
| 3,906,938 | 9/1975 | Fleischhacker . | |
| 4,538,622 | 9/1985 | Samson et al. | 128/772 |
| 4,545,390 | 10/1985 | Leary | 128/772 |
| 4,846,186 | 7/1989 | Box et al. | 128/657 |
| 4,922,924 | 5/1990 | Gambale et al. | 128/772 |
| 5,259,393 | 11/1993 | Corso, Jr. et al. | 128/772 |
| 5,267,574 | 12/1993 | Viera et al. | 128/772 |
| 5,353,808 | 10/1994 | Viera | 128/772 |
| 5,551,444 | 9/1996 | Finleyson | 128/772 |

*Primary Examiner*—Max Hindenburg
*Attorney, Agent, or Firm*—Henry W. Collins

[57] ABSTRACT

A flexible guidewire having a radiopaque marker at its distal end. The marker is defined by a platinum band attached to a reduced diameter portion of a guidewire core wire. A flexible spring overlies the radiopaque marker bank. The spring is constructed of stainless steel. A weld band is formed at the distal end of the core wire and is fused to the distal end of the marker band to thereby cause these elements to be fused into a single unitary structure.

6 Claims, 1 Drawing Sheet

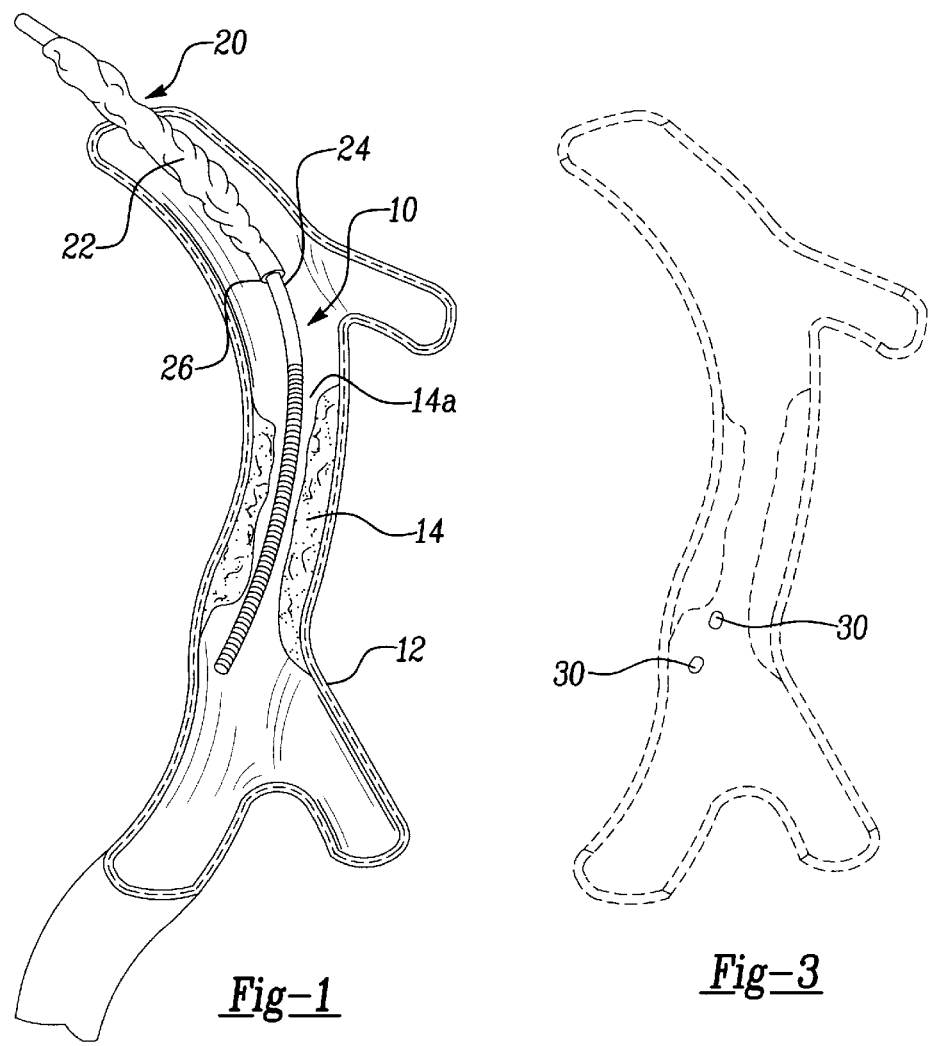
Fig-1
Fig-3
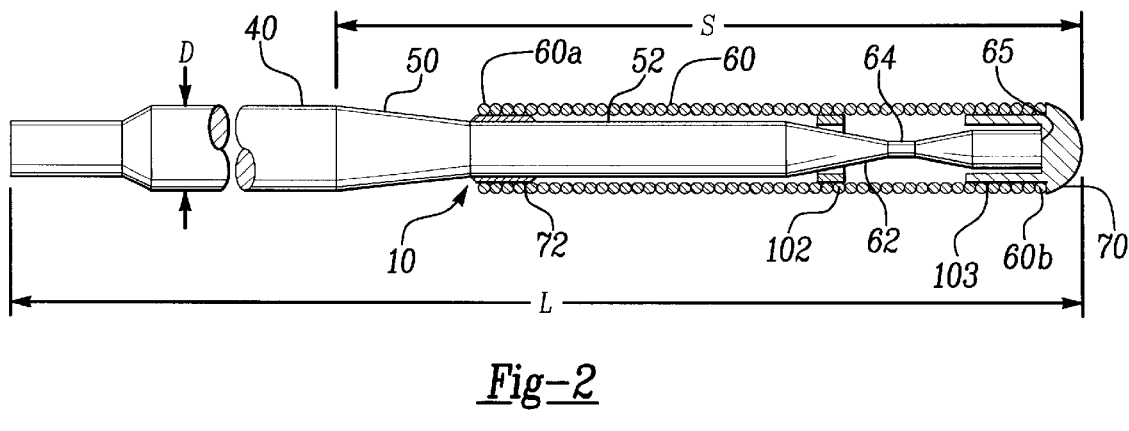
Fig-2

GUIDEWIRE HAVING RADIOPAQUE DISTAL TIP

FIELD OF THE INVENTION

This invention relates to a guidewire used to position a balloon catheter within a blood vessel of a human subject, and more particularly, to a guidewire having an integral marker segment and distal tip at the distal end of the guidewire.

BACKGROUND ART

The medical procedure of coronary angioplasty can increase blood flow through the coronary artery system. This procedure may sometimes be used as an alternative to coronary bypass surgery. A catheter having a deflated balloon at its distal end is guided through the cardiovascular system to the coronary artery of the heart. The balloon is inflated to compress deposits which have accumulated along the inner walls of the coronary artery to thereby widen the artery lumen and increase blood flow.

One technique for positioning the balloon catheter is that of using an elongated flexible guidewire which is inserted into the vessel of a patient and used to guide the balloon catheter into the vessels.

The guidewire passes through a tortuous or winding path as it is inserted into the subject. The distal tip is flexible to avoid damaging inner walls of the blood vessels that the guidewire tip contacts along the winding path. The distal tip is often pre-bent to a desired configuration so that the guidewire can be inserted into the branching blood vessels along the path. When the tip is pre-bent the physician must be able to orient the tip so it can be pushed into these branching blood vessels.

Prior art patents which disclose flexible, elongated guidewires are U.S. Pat. No. 4,545,390 to Leary, U.S. Pat. No. 4,538,622 to Samson et al. and U.S. Pat. No. 3,906,938 to Fleischhacker. U.S. Pat. No. 4,846,186 to Box et al. is assigned to the assignee of the present application and is incorporated herein by reference.

One problem with currently available guidewires concerns the visibility of the guidewire and in particular the visibility of the distal tip of the guidewire. If the guidewire is fully opaque on an x-ray or fluoroscopy viewing screen, it may hinder positioning the balloon catheter which must also be radiopaque. Also, such fully opaque guidewires may hinder viewing of post angioplasty angiograms used in studying the effects the angioplasty procedure had on the treated vessel. Guidewires that have opaque markers spaced back from the tip do not adequately depict the exact position of the tip on the viewing monitor.

U.S. Pat. No. 4,922,924 to Gambale et al. discloses a guidewire for use with a balloon catheter. The guidewire includes a coil assembly that is formed from a highly radiopaque coil and a non-radiopaque coil, arranged in bifilar arrangement to define a moderate radiopacity guidewire section. U.S. Pat. Nos. 5,259,393 to Viera et al.; 5,267,574 to Viera et al. and 5,353,808 to Viera, Viera being the applicant of the present invention, are all directed toward guidewire systems having radiopaque markers.

Another problem with guidewires having a radiopaque markers at the distal tip of the guidewire is that it is very difficult to secure the radiopaque marker to the guidewire so that the marker remains attached to the guidewire.

SUMMARY OF THE INVENTION

The present invention relates to an elongated flexible guidewire designed for insertion into blood vessel to aid in the positioning of a balloon catheter within the blood vessel.

An elongated flexible guidewire constructed in accordance with the invention includes a core wire having a uniform first diameter portion extending to a distal portion of the guidewire where the core wire tapers to a second lesser diameter portion shorter than the first diameter portion. A flexible coiled wire spring extends over the length of a distal portion of the core wire and is attached at either of its ends to the core wire. A highly radiopaque marker band is interposed between the coiled wire spring and the core wire at the distal end of the core wire to increase the visibility of the guidewire at the distal end of the guidewire. A hemispherical weld bead is bonded to the core wire, the coiled wire and marker band to form a unitary structure.

In accordance with a preferred construction the flexible coil spring is constructed from stainless steel and it extends over the highly radiopaque marker band that is mounted on the core wire. The marker band is formed from highly radiopaque platinum that is visible through the coil when viewed on an x-ray viewing monitor.

As the stainless steel segment is wound, the pitch of the winding over the marker band is altered to leave gaps between adjacent coils. The highly radiopaque marker band is visible beneath these gaps.

From the above it is appreciated that one object of the invention is a flexible guidewire having improved visibility at the very distal end of the guidewire. Also, the radiopaque marker band is formed as a unitary structure with the core wire and the distal tip of the guidewire in order to fixedly secure those elements to each other. This and other objects, advantages and features of the invention will become better understood from a detailed description of the invention which is described in conjunction with the accompanying drawings.

BRIEF DESCRIPTION OF THE DRAWINGS

FIG. 1 is a diagrammatic view showing a blood vessel that has been occluded with deposits along an inner wall and shows the positioning of a flexible guidewire and balloon catheter mounted on the guidewire within a blood vessel;

FIG. 2 is an elevation segmented view of a flexible guidewire core wire constructed in accordance with the invention; and FIG. 3 is a view of a flexible guidewire constructed in accordance with the invention as it appears when viewed on a fluoroscopic viewing screen.

DESCRIPTION OF THE PREFERRED EMBODIMENT(S)

FIG. 1 illustrates a distal portion of a flexible, small diameter guidewire 10 that can be guided through the cardiovascular system of a patient. A distal end of the guidewire is shown in FIG. 1 approaching a region in a blood vessel 12 having occlusions 14 which restricts blood flow through the blood vessel 12. The guidewire 10 is long enough to be routed from a patient entry point through the vessel to the obstructed blood vessel region. In a preferred embodiment the guidewire has a length L of 175 cm. (approximately 69 inches). As the guidewire 10 is inserted along the tortuous path to the obstructed blood vessel region, an attending physician conducting the procedure monitors progress of the guidewire 10 on a viewing screen.

FIG. 1 also illustrates the use of a guidewire for routing a balloon catheter 20 to the vicinity of the obstructions 14. The balloon catheter 20 includes a passageway or lumen that extends from a proximal location outside the patient to a distally located balloon 22. Fluid is routed into the catheter through this lumen to inflate the balloon 22. A distal tip portion 24 of the catheter 20 includes a marker band 26 to aid the attending physician in monitoring balloon catheter progress as it is positioned within the patient. A second, center passageway or lumen in the catheter 20 has a diameter sufficient to accommodate the guidewire 10 so that once the guidewire is properly positioned within the subject, the catheter 20 can be slid over the guidewire.

The distal tip portion of the guidewire 10 is flexible and can be bent to a predetermined configuration to facilitate routing the guidewire 10 along the cardiovascular system to the occluded region of the blood vessel 12. The pre-bent tip can be re-oriented by the physician. Torque applied to the proximal end of the guidewire is transmitted along the length of the guidewire to orient the distal tip to point in a desired direction.

In use, a distal end of the guidewire 10 is routed through a narrow passageway 14*a* in the obstruction 14 and the balloon catheter 20 slipped over the guidewire until the balloon 22 bridges the region 14 of obstructions within the blood vessel 12. The balloon 22 is then inflated and the outer surface of the balloon contacts the obstruction 14. The inner walls of the obstruction 14 are compressed or sometimes fractured and a wider lumen or passageway is created in the blood vessel 12.

As described in detail below, the guidewire 10 is constructed so that bands or regions 30 of high radiopaqueness appear when the blood vessel 12 is monitored on a viewing screen. The bands 30 are separated at a fixed distance thereby giving a reference length. The opacity of the bands 30 can be varied and in such an embodiment to allow adequate tracing of the guidewire while minimizing interference with a post procedure angiogram.

Turning now to FIG. 2, the guidewire 10 is seen to include a center stainless steel wire core 40 having a first uniform diameter D, in the range 0.0130–0.035 inch, extending well over half the length "L" of the guidewire. To improve the depiction of details of the distal portion of the guidewire 10, this uniform diameter elongated portion has been sectioned and a major portion of its length deleted from FIG. 2.

The total length of the uniform diameter portion 40 is approximately 148 cm. of the total guidewire length "L" of 175 cm. It is typically covered with a suitable coating to make its outer surface lubricious. A short proximal portion of the core 40 is not coated to allow for easier handling by the physician. The remaining distal segment of the guidewire has a length "S" of approximately 27 cm.

At the distal end of the guidewire, the wire core 40 tapers along a portion 50 uniformly to a portion 52 having a uniform diameter D'. A coiled wire spring 60 covers a distal portion of the core wire. The core 40 is again tapered uniformly along a segment 62. The next most distal segment 64 of the core 40 is flattened and is also surrounded by the tightly coiled portion of the spring 60. This next most distal segment of the guidewire 10 has a length of approximately 1 inch and can be pre-bent to a particular configuration by the attending physician to facilitate insertion of the guidewire within the subject.

At the extreme distal tip portion of the guidewire 10, a weld bead 70 is bonded to the distal portion 60*b* of the spring 60, to the distal cylindrical portion 65 of the core wire. The weld defines a smooth hemispherical bead which does not damage the inner lining of the blood vessels as the guidewire tip comes in contact with those linings.

The spring 60 is soldered to the core 40 using, Surgical Grade Solder. One solder connection 72 joins the proximal spring portion 60*a* and the intermediate cylindrical portion. The core 40 is constructed from a uniform diameter stainless steel wire which is centerless ground along the tapered segments to the reduced diameter segments. The flattened portion 64 is formed by rolling or stamping a uniform diameter core portion having an initial diameter of 0.0025 inch which when flattened by a die, results in 0.0018 inch thick by 0.0045 inch wide flattened portion that "bulges" outward on two sides.

The spring 60 is closely packed along the entire length except for the distal tip of the spring so that adjacent coils of the spring 60 touch each other. The coil 60 overlies high radiopaque bands or rings 102, 103. The bands 102, 103 are preferably platinum metal and are spaced apart a fixed distance and provide a length reference for a physician viewing the core wire 10 on a viewing screen. Each band 102, 103 on the core wire corresponds to a band 30 on the viewing screen depicted in FIG. 3.

The next most distal segment 66 of the core wire 40 extending from the flattened portion 64 is tapered outwardly and this segment terminates in the uniformly cylindrical segment 65 of a slightly smaller diameter than the diameter of either of the other cylindrical segments 40,52

During fabrication of the guidewire 10, the band 102 is slipped over the core wire and attached by soldering to the core wire 40. A final distal band 103 is slipped over the core wire and soldered to the core wire 40. The separation between bands 102 can be adjusted depending upon the intended use of the guidewire. In a preferred embodiment, the separation is the same between adjacent bands and is determined by the number of coils in the coil segments 104. Preferably, the marker bands are formed of platinum, however, it is desired to have the radiopacity of the visible bands 30 lighter, a different alloy or material is utilized for different bands 102.

Upon applying the weld bead 70 to the core wire the heat of welding causes the distal end of the platinum marker band 103 to melt and the distal end of the stainless steel spring to melt thereby fusing these three elements together to form a single unitary structure.

The guidewire 10 depicted in FIG. 2 is particularly suited for insertion into small diameter blood vessels and can be used, for example, for positioning a balloon in a bridging relationship within the coronary artery.

FIG. 3 illustrates the image of the guidewire 10 which a physician would see while using the guidewire during angioplasty. Unlike a fully radiopaque guidewire, the bands 30 are visible at spaced locations to aid the physician during the angioplasty while not interfering with a post procedure angiogram. The bands 30 are spaced at one-half inch intervals to provide a reference for the physician with regard to positioning the guidewire 10 within the blood vessel 12.

The dimensions mentioned in this specification are for a preferred embodiment in the invention for use in small diameter blood vessels. These dimensions are representative of this use and are not intended to limit the invention, but rather define a small diameter guidewire whose characteristics are particularly advantageous. It is the intent, however, that the invention include all modifications and/or alterations from the disclosed dimensions and design falling within the spirt or scope of the appended claims.

What is claimed is:

1. A guidewire having a radiopaque distal tip comprising:
   a) an elongated core wire including a first, uniform diameter cylindrical core wire portion and a second more flexible, reduced diameter core wire portion at the distal end of said uniform diameter portion;

b) a coiled wire spring having distal and proximal ends attached to the core wire and extending from the uniform diameter portion to the distal end of the reduced diameter portion of the core wire;

c) a cylindrical band formed of a highly radiopaque material interposed between the coiled wire spring and the core wire and extending from the distal end of the core wire along the flexible portion of the core wire and being of a length which is substantially shorter than the length of the flexible portion of the core wire; and, d) a weld bead fused to the distal end of the core wire, the distal end of the cylindrical band and the distal end of the coiled spring, to thereby provide a single unitary structure.

2. The guidewire of claim 1 wherein the reduced diameter portion of the core wire includes a flattened portion which extends distally from the first uniform diameter portion, and a second uniform cylindrical diameter portion which extends distally from the flattened portion wherein said radiopaque band is mounted on the second uniform cylindrical portion of the core wire.

3. The guidewire of claim 2 wherein the diameter of the second uniform cylindrical portion of the guidewire is less than the diameter of the first uniform cylindrical portion of the guidewire.

4. The guidewire of claim 1 wherein the reduced diameter portion includes a first tapered portion which extends distally from the first uniform diameter portion, a second uniform diameter cylindrical portion having a diameter which is smaller than the diameter of the first uniform portion and which extends distally from the first tapered portion, a second tapered portion which extends distally from the second uniform diameter cylindrical portion, a flattened portion which extends distally from the second tapered portion, a third tapered portion which extends distally from the flattened portion, and a third uniform diameter portion which extends distally from the third tapered portion wherein said radiopaque band is mounted on said third uniform diameter portion.

5. The guidewire of claim 4 wherein the diameter of the second uniform diameter cylindrical portion is smaller than the diameter of the first uniform diameter cylindrical portion and the third uniform diameter cylindrical portion is smaller than the diameter of the second uniform diameter cylindrical portion.

6. The guidewire of claim 1 including a second cylindrical band formed of a highly radiopaque material and being of a length which is substantially shorter than the length of the flexible portion of the core wire, said second cylindrical band being interposed between the coil wire spring and the core wire and being spaced apart from said first cylindrical band by a predetermined distance.

* * * * *